US009207152B2

(12) United States Patent
Nogami et al.

(10) Patent No.: US 9,207,152 B2
(45) Date of Patent: Dec. 8, 2015

(54) PRETREATMENT APPARATUS AND MASS ANALYZING APPARATUS EQUIPPED WITH THE SAME

(75) Inventors: Makoto Nogami, Tsuchiura (JP); Katsuhiro Kanda, Hitachinaka (JP); Izumi Waki, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 102 days.

(21) Appl. No.: 13/377,154

(22) PCT Filed: Jun. 24, 2010

(86) PCT No.: PCT/JP2010/060727
§ 371 (c)(1),
(2), (4) Date: Dec. 27, 2011

(87) PCT Pub. No.: WO2010/150842
PCT Pub. Date: Dec. 29, 2010

(65) Prior Publication Data
US 2012/0079875 A1    Apr. 5, 2012

(30) Foreign Application Priority Data

Jun. 25, 2009    (JP) ................................. 2009-151442

(51) Int. Cl.
*G01N 33/48* (2006.01)
*G01N 1/40* (2006.01)
*G01N 35/02* (2006.01)
G01N 30/00 (2006.01)
H01J 49/00 (2006.01)

(52) U.S. Cl.
CPC ............ *G01N 1/4055* (2013.01); *G01N 35/025* (2013.01); *G01N 2001/4061* (2013.01); *G01N 2030/009* (2013.01); *H01J 49/00* (2013.01)

(58) Field of Classification Search
None
See application file for complete search history.

(56) References Cited

U.S. PATENT DOCUMENTS

| 5,585,068 A * | 12/1996 | Panetz et al. .................... 422/64 |
| 5,660,727 A * | 8/1997 | Gleave et al. ................. 210/141 |
| 2002/0122745 A1* | 9/2002 | Takase et al. ................... 422/63 |
| 2011/0157580 A1* | 6/2011 | Nogami et al. ................ 356/36 |

FOREIGN PATENT DOCUMENTS

| JP | 01-174968 | 7/1989 |
| JP | 5-80059 | 3/1993 |
| JP | 11-201953 | 7/1999 |
| JP | 2001-74719 | 3/2001 |
| JP | 2004-93194 | 3/2004 |
| JP | 2006-7081 | 1/2006 |

OTHER PUBLICATIONS
Office Action issued in Chinese Patent Application No. 201080026060.0 on Oct. 21, 2013.

* cited by examiner

*Primary Examiner* — P. Kathryn Wright
(74) *Attorney, Agent, or Firm* — Baker Botts L.L.P.

(57) ABSTRACT

A biological sample preprocessing apparatus includes solid-phase extraction cartridges which purify/concentrate specific constituents of a biological sample, cartridge holders which hold one of the solid-phase extraction cartridges, a cartridge transport that carries the cartridge holders along a continuous track surface, a sample probe that discharges the biological sample into the solid-phase extraction cartridge held in the cartridge holders, a water-based solvent probe that discharges a water-based solvent into the solid-phase extraction cartridge held in the cartridge holder, an organic solvent probe that discharges an organic solvent into the solid-phase extraction cartridge held in the cartridge holder, a pressure loader that applies an air pressure load to the solid-phase extraction cartridge held in the cartridge holder, and a control unit that controls operation of the cartridge transport, the sample probe, the solvent probes, and the pressure loader, wherein sample addition and solvent addition alternate with pressure loading.

3 Claims, 6 Drawing Sheets

* : DENOTES THE SUBSTEP NUMBER SHOWN IN FIG. 3.

PRETREATMENT APPARATUS AND MASS ANALYZING APPARATUS EQUIPPED WITH THE SAME

TECHNICAL FIELD

The present invention relates to a pretreatment apparatus that assays constituents contained in a biological sample of blood and serum or the like, and a mass analyzing instrument equipped with the same.

BACKGROUND ART

To analyze any trace compounds, e.g., drugs, contained in a biological sample, such as blood and serum or the like, it is necessary to purify and concentrate the compounds, since the constituents to be assayed are in very small quantities.

One method often used to efficiently purify and concentrate compounds is automated solid-phase extraction, where an apparatus is desired that is more compact, capable of conducting a larger number of types of analyses, and higher in throughput. Solid-phase extraction is a method of separating, purifying, and concentrating an analyte (or a substance to be assayed), by retaining this substance in a solid phase extracting agent (e.g., a plurality of small beads or membrane-like substances) in packed form in a small container such as a minicolumn or cartridge, then washing the solid phase extracting agent, and collecting desired compounds from the solid phase extracting agent.

The step of collecting the desired compounds by the solid phase extraction includes five process steps: (1) a solid-phase extracting agent conditioning step in which to pass an organic solvent through the solid phase extracting agent, (2) a solid-phase equilibrating step in which to pass a water-based solvent through the solid phase extracting agent, (3) the step of retaining the analyte in the solid phase extracting agent by passing the sample through the solid phase extracting agent, (4) a washing step in which to pass water through the solid phase extracting agent, and (5) the step of passing the organic solvent through the solid phase extracting agent and eluting the analyte from the solid phase.

An example of an automatic solid-phase extraction apparatus is described in Patent Document 1, for example. The automatic solid-phase extraction apparatus described therein includes a vacuum rack equipped with a multiple solid-phase plate bank, a dispensing head that suctions and discharges a liquid, and means that transfers the dispensing head.

The above conventional extraction apparatus enables a batch-processing (using 96 holes plate) capability and an ability to purify and concentrate analyte constituents in blood, serum, and the like, automatically. The solution containing purified and concentrated analytes, thus obtained, are transferred to a liquid-chromatography or a mass spectrometry instrument for qualitative and quantitative analyses of the trace analyte substances, e.g., drugs, contained in the biological sample, such as blood and serum or the like.

This technique adopted in the conventional extraction apparatus is effective in that conventional manual pretreatment by the analyzing person prior to mass spectrometry has been automated, so as to accelerate significant reduction in time and in statistical variations in data.

RELATED ART LITERATURE

Patent Documents

Patent Document 1: JP-2006-7081-A

SUMMARY OF THE INVENTION

Problems to be Solved by the Invention

Under the apparatus configuration described in Patent Document 1, however, dispensing tips are changed in each step of solvent suctioning and discharging, moving the dispensing head to a dispensing tip container by the transfer means.

In the scheme of the conventional technique, therefore, the solid-phase extraction steps use multiple kinds of solvents (a water-based solvent and an organic solvent). For example, step (1) discussed above uses the organic solvent and step (2) uses the water-based solvent. This has required changing dispensing tips with each change of the kind of solvent, thus causing increases in the quantity of dispensing tips discarded and in costs of consumables. In addition, since the dispensing head needs to move among tip-mounting position, solvent-suctioning position, and solvent-discharging position, it takes a long time to move, resulting in an extended cycle time and hence in reduced throughput.

Furthermore, since the dispensing head is of multiple tip construction and thus since the apparatus is constructed to conduct successive solid-phase extracting operations by using a plurality of samples of the same kind at the same time, a plurality of tips need to be mounted on the dispensing head to perform solid-phase extraction of one sample, for example. Accordingly, solvents as many as dispensing tips were actually discarded, resulting in unnecessary waste of consumables.

Moreover, since only solvents of the same kind can be selected at a time in the step of suctioning or discharging the reagent placed on a solid-phase extraction plate, it is impossible to pack the well with multiple solvents at the same time and consequently to conduct a multi-analyte process that uses different solvents.

Furthermore, during suctioning with the vacuum rack mounted on the solid-phase extraction plate, no other operations are executable, and once a process has been started, one cannot start subsequent processing of another sample until the ongoing process is completed. That is to say, applications of the conventional technique lack flexibility of processing operation.

An object of the present invention is to achieve a pretreatment apparatus using a minimum number of consumables and capable of conducting multi-item separation and purification of an analyte in a series of solid-phase extraction steps with high efficiency. Another object is to achieve a mass analyzing apparatus equipped with the pretreatment apparatus.

Means for Solving the Problems

In order to attain the above objects, the present invention is configured as follows.

The present invention comprises a biological sample pretreatment apparatus, that includes a solid-phase extraction cartridge that purifies and concentrates only specific constituents contained in a biological sample, cartridge holder that holds the solid-phase extraction cartridge, cartridge transport means that carries the cartridge holder along a continuous track, a sample probe that discharges the biological sample into the solid-phase extraction cartridge held in the cartridge holder, a water-based solvent probe that discharges a water-based solvent into the solid phase extraction cartridge held in the cartridge holder, an organic-solvent probe that discharges an organic solvent into the solid phase extraction cartridge held in the cartridge holder, a pressure loader that applies an air pressure load to the solid phase extraction cartridge held in the cartridge holder, and a control unit that controls operation of the cartridge transport means, the sample probe, the water-based solvent probe, the organic-solvent probe, and the pressure loader.

Effects of the Invention

This invention achieves a pretreatment apparatus, and a mass analyzing instrument using the same, that requires a minimum amount of consumables and can conduct separation and purification of a plurality of analytes through consecutive solid-phase extraction steps with high efficiency.

MODE FOR CARRYING OUT THE INVENTION

A trend towards the application of mass spectrometry to clinical sites is increasing in recent years. In an automatic analyzer based on the conventional immunoassay technique that utilizes antigen-antibody reactions, cross reactions pose problems associated with the reliability of data accuracy. In contrast to this, mass spectrometry enables highly accurate discrimination without cross reactions, since the mass of a substance to be assayed is used as the basis for measurement. That is why the use of mass spectrometry in clinical applications is increasing.

Mass spectrometry is a technique that enables discrimination between structurally similar molecules, e.g., metabolites. In particular, an MS/MS analytical method and an $MS^n$ analytical method enable highly accurate discrimination between structurally similar constituents, since the masses of both a substance to be assayed and a substance obtained by fragmenting the analyte can be analyzed using either method. For clinical application of mass spectrometry, the pretreatment (purification/concentration) of a sample is prerequisite, such as solid-phase extraction or the like. Increasingly, it is desired to fully automate all process steps from pretreatment of the sample to analysis and testing in clinical applications.

In response to this trend, an embodiment of the present invention is of a configuration that enables automation in all process steps from pretreating a sample to analyzing and testing the sample.

Hereunder, an embodiment of an automatic analyzer according to the present invention will be described referring to the accompanying drawings. The embodiment described hereunder is just an example of the invention and it is therefore to be understood that the embodiment does not limit the invention.

FIRST EMBODIMENT

Figure 1:
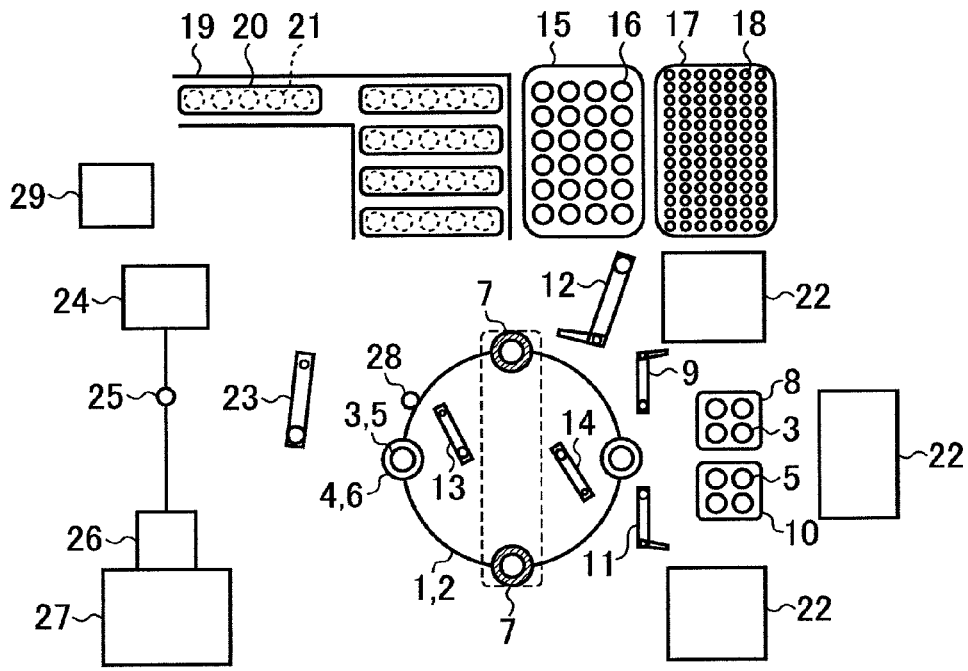
FIG. 1 is a schematic configuration diagram of an automatic analyzer to which an embodiment of the present invention is applied.
Figure 2:
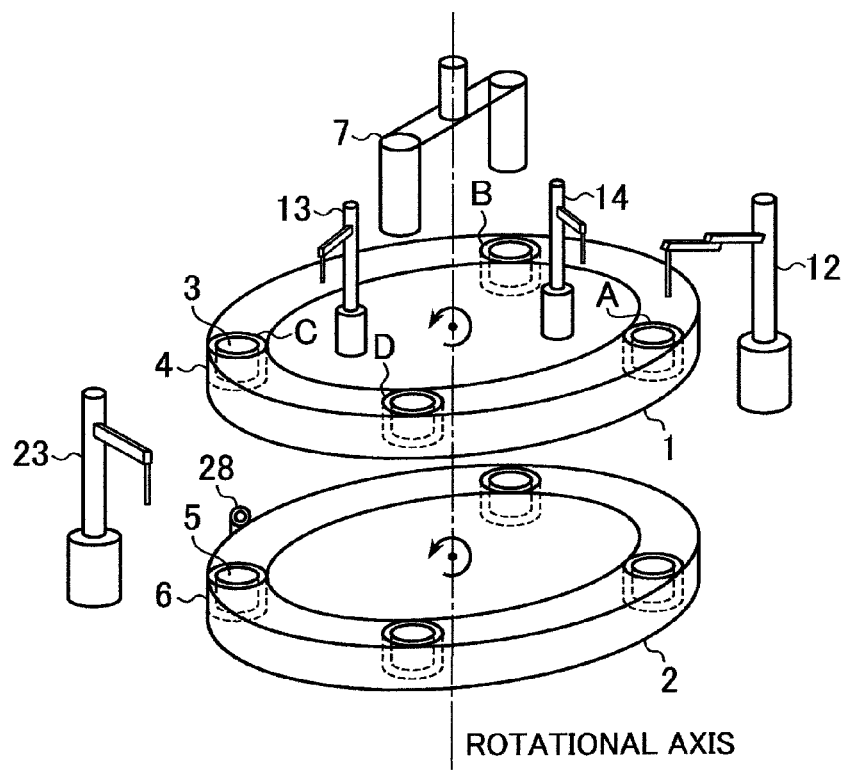
FIG. 2 is an enlarged schematic view of a solid-phase extraction unit of the automatic analyzer shown in FIG. 1.

FIG. 1 is a conceptual diagram (top view) of the automatic analyzer applying the present invention, and FIG. 2 is a conceptual diagram of a solid-phase extraction unit, in particular, in the embodiment of FIG. 1.

First, a configuration of the solid-phase extraction unit in the first embodiment of the present invention is described below referring to FIGS. 1 and 2.

Here, solid phase extraction cartridges may contain different kinds of beads, enabling a plurality of modes of extraction. Analyzing accuracy can be improved by selecting an appropriate mode according to material properties of a sample to be extracted, and repeating a plurality of solid-phase extraction processes.

The solid-phase unit in the present invention, shown in FIG. 2, includes solid phase extraction cartridges 3 that each purify and concentrate only specific constituents contained in a biological sample, e.g., whole blood and serum or the like, cartridge holders 4 that each hold one of the solid phase extraction cartridges 3, cartridge transfer means 1 adapted for carrying the cartridge holder 4 along a continuous track (in the illustrated example, a rotary track), pressure loaders 7 that applies a pressure load to the cartridge holders 4, receiving trays 5 that each receive an eluted extract from the solid phase extraction cartridge 3, receiving tray holders 6 that each hold one of the receiving trays 5, receiving tray transport means 2 that carries each receiving tray holder 6, a sample probe 12 that suctions and discharges a sample and a reagent, a water-based solvent probe 13 that discharges a water-based solvent, an organic solvent probe 14 that discharges an organic solvent, an eluate probe 23 that suctions/discharges the eluted extract and introduces the eluate into a mass analyzer, and a washing port 28 that washes the eluate probe 23.

The cartridge holder 4 formed in the cartridge transport means 1 of an annular shape has an opening at an upper surface thereof to accept and accommodate the solid phase extraction cartridge 3 to be inserted, and has at a lower surface thereof an opening smaller in diameter than that of the solid phase extraction cartridge 3. The cartridge holder 4 is constructed to support the solid phase extraction cartridge 3 so that a solution can drip downward from the lower surface of the solid phase cartridge 3, which solution, e.g., can be a extracted solution and the like from the cartridge 3.

The pressure loaders 7 are each contained in one of two cylinders, and respective pistons of the pressure loaders apply an air pressure in a downward direction, that is, towards the solid phase extraction cartridges 3 held in the cartridge holders 4.

Next, a total configuration of the automatic analyzer, except for the solid-phase extraction unit shown in FIG. 2, is described below in accordance with FIG. 1.

Referring to FIG. 1, the total configuration of the automatic analyzer includes a cartridge storage unit 8 for storage of the solid phase extraction cartridges 3, a cartridge transport arm 9 that carries the solid phase extraction cartridges 3 from the cartridge storage unit 8 to the cartridge holders 4, a receiving tray storage unit 10 for storage of the receiving trays 5, a receiving tray transport arm 11 that carries the receiving trays 5 from the receiving tray storage unit 10 to the receiving tray holders 6, a sample transport mechanism 19 that carries a rack 20 with sample containers 21 placed therein, a reagent storage unit 15 for storage of reagent containers 16 each containing an internal standard substance appropriate for a substance to be assayed, a tip storage unit 17 for storage of disposable dispensing tips 18, discarding ports 22 for discarding used disposable parts such as used dispensing tips 18 or used solid phase extraction cartridges 3 or used receiving trays 5, an eluate injection unit 25 that injects an eluate into a flow path to which a solution is supplied from a pump 24 to a mass analytical unit 27, an ionizer 26 that ionizes the substance to be assayed, the mass analytical unit 27 that analyzes the analyte (the substance to be assayed) on a mass-to-charge (m/z) ratio basis, and a control unit 29 that controls operations, such as the operation of the solid-phase extraction unit and the like.

The cartridge transport means 1 and the receiving tray transport means 2 share one rotational axis, and the cartridge transport means 1 is disposed over the receiving tray transport means 2. Four cartridge holders 4 are formed in the cartridge transport means 1, and four receiving tray holders 6 in the receiving tray transport means 2. Each of the four cartridge holders 4 can be positioned to form a mutually-facing pair with a corresponding receiving tray holder 6, so that the solution that has been extracted or discharged, or the like, from one solid phase extraction cartridge 3 held in one cartridge holder 4 is stored into one receiving tray 5 held in one receiving tray holder 6.

Next, a configuration of the control unit 29 is described below with reference being made, to FIG. 4.

Figure 4:
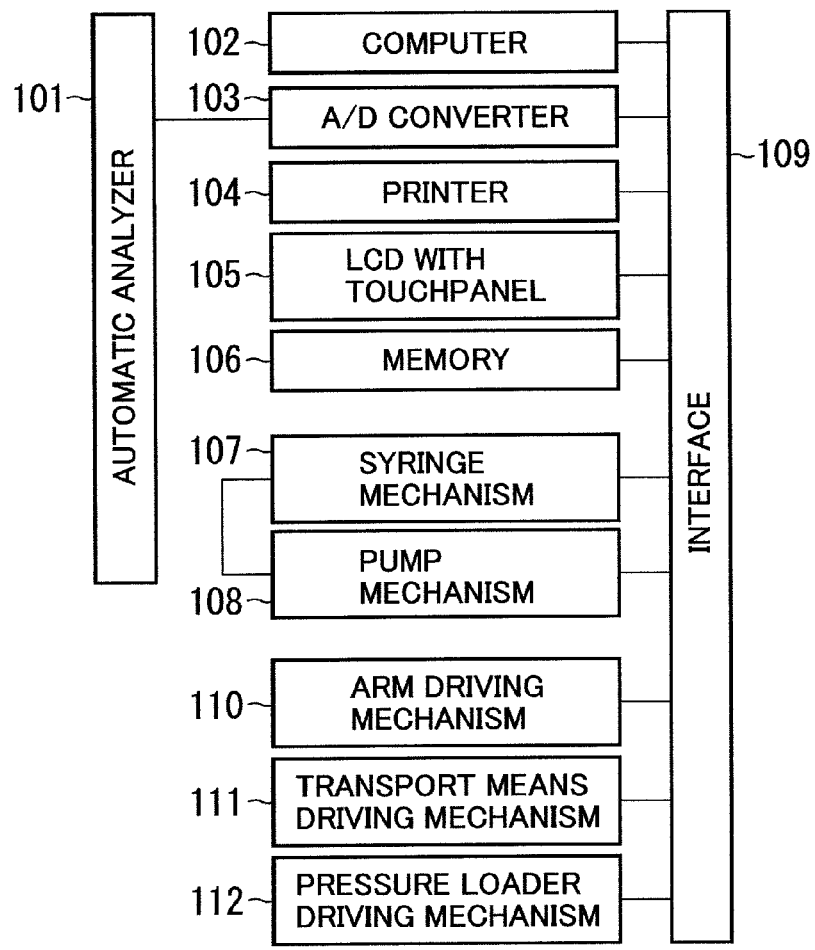
FIG. 4 is a functional block diagram of a control unit of the automatic analyzer shown in FIG. 1.

Referring to FIG. 4, information that has been obtained with the mass analytical unit 27 of the automatic analyzer 101 flows through an A/D converter 103 first and then an interface 109, and enters a computer 102 in which a concentration of the analyte is calculated. Analytical results on the analyte, based on the calculated concentration, are printed out onto a printer 104 or displayed on an screen of an LCD 105 equipped with a touch panel, via the interface 109. The analytical results are also stored into a memory 106. The interface 109 is also connected to a syringe mechanism 107 and a pump mechanism 108, and can control the solution suctioning and discharging operation of the sample probe 12, water-based solvent probe 13, organic solvent probe 14, and eluate probe 23.

In addition, an arm-driving mechanism 110 for driving the cartridge transport arm 9 and the receiving tray transport arm 11, a driving mechanism 111 for the cartridge transfer means 1 and the receiving tray transport means 2, and a driving mechanism 112 for the pressure loader 7 are connected to the computer 102 via the interface 109. Operation of each of these mechanisms is controlled by the computer 102.

A procedure relating to the analysis using the automatic analyzer in the first embodiment of the present invention is explained below referring to FIG. 3. The procedure will be explained in a sequence, which is in accordance with a sequence of the five process steps of solid-phase extraction, followed by a measuring step in a mass analytical unit.

Figure 3:
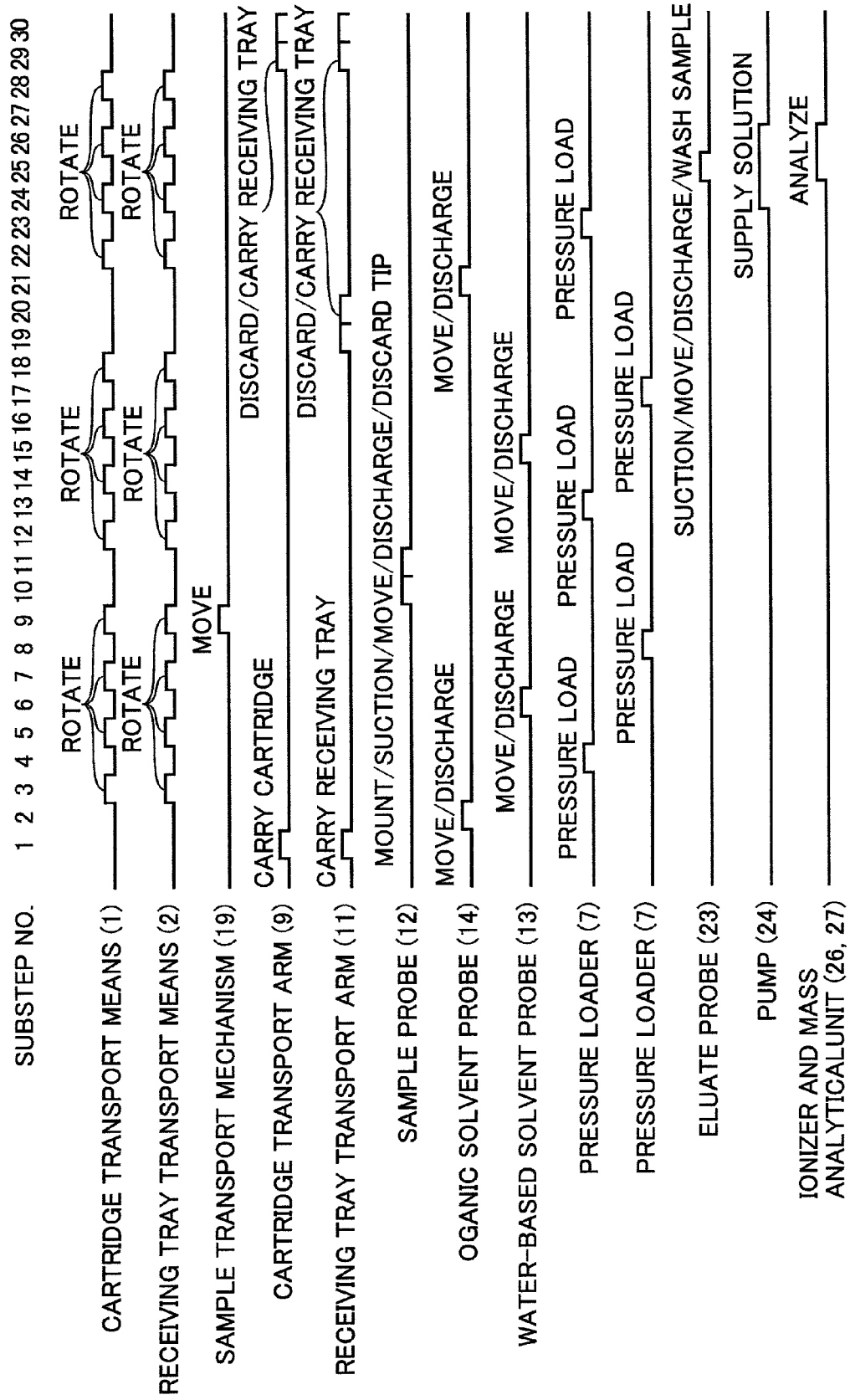
FIG. 3 is a diagram showing a progress pattern of analytical steps in the embodiment of the present invention.

FIG. 3 is a diagram showing a temporal sequence pattern of the analytical steps. More specifically, the five process steps in a solid-phase extraction are: (1) a solid phase extraction agent conditioning step to pass the organic solvent, through a solid phase extraction agent, (2) a solid phase extraction agent equilibrating step to pass the water-based solvent through the solid phase extraction agent, (3) the step of retaining the analyte in the solid phase extraction agent by passing the sample through the solid phase extraction agent, (4) a washing step to pass water through the solid phase extraction agent, and (5) the step of passing the organic solvent through the solid phase extraction agent and eluting the analyte from the solid phase extraction agent.

First, the solid phase extraction agent conditioning step to pass the organic solvent through a solid phase extraction agent is described below. The operation described below is controlled primarily by the control unit 29.

One of the solid-phase cartridges 3 held in the cartridge storage unit 8, and one of the receiving trays 5 in the receiving tray storage unit 10 are mounted in an empty cartridge holder 4 and an empty receiving tray holder 6, respectively, by the cartridge transport arm 9 and the receiving tray transport arm 11, respectively.

The organic solvent probe 14 then discharges methanol into the solid phase extraction cartridge 3 mounted in the cartridge holder 4. This step is conducted at position A shown in FIG. 2. A plurality of solid phase extraction cartridges 3 are provided, each packed with extraction agent for extraction modes of either reverse-phase, normal-phase, a ion exchange, size exclusion, or mixed modes, which are s held in the cartridge storage unit 8. When a user enters a desired analyte on a screen of the LCD 105 equipped with a touch panel, measuring parameters (assay parameters) prestored for various substances will be called up from the memory 106 via the interface 109 and an appropriate solid phase extraction cartridge 3 will be selected.

Next, the cartridge transport means 1 rotates. Thus, the cartridge holder 4 holding the solid phase extraction cartridge 3 to which methanol has been added moves to position B shown in FIG. 2. At this time, the receiving tray transport means 2 positioned below the cartridge transport means 1, also rotates coaxially and the cartridge holders 4 and the receiving tray holders 6 move maintaining respective relative positions.

The pressure loader 7 positioned over positions B and D in FIG. 2, moves downward to the cartridge holder 4 at position B and applies an air pressure load to pass the methanol into the solid phase extraction cartridge 3 in which the solid phase is then conditioned. A waste liquid of the passed methanol will remain in the receiving tray 5.

Next, the solid phase extraction agent equilibrating step to pass the water-based solvent through the solid phase extraction agent is described below. The cartridge transport means 1 rotates for the cartridge holder 4 holding the solid phase extraction cartridge 3 to reach position C shown in FIG. 2. In this step as well, similarly as above, the cartridge holders 4 and the receiving tray holders 6 move maintaining the respective relative positions.

After this, the water-based solvent probe 13 then discharges water into the solid phase extraction cartridge 3 containing the conditioned solid phase extraction agent. The cartridge transport means 1 then rotates for the cartridge holder 4 holding the solid phase extraction cartridge 3 to reach position D. At this time, similarly as above, the cartridge holders 4 and the receiving tray holders 6 move maintaining the respective relative positions. The pressure loader 7 positioned over positions B and D, moves downward to the cartridge holders 4 at position D and applies an air pressure load to pass the water into the solid phase extraction cartridge 3 in which the solid phase extraction agent is then equilibrated. A waste liquid of the passed water will remain in the receiving tray 5.

Next, the step of retaining the analyte in the solid phase extraction agent by passing the sample through the solid phase extraction agent is described below. The cartridge transport means 1 rotates for the cartridge holder 4 holding the solid phase extraction cartridge 3 to reach position A. At this time, similarly as above, the cartridge holders 4 and the receiving tray holders 6 move maintaining the respective relative positions. Next, the sample probe 12 moves to a position over the tip storage unit 17 and, this position, one dispensing tip 18 is then mounted on the sample probe 12. The sample probe 12 with the mounted dispensing tip 18 moves to a position above one reagent container 16 from which the sample probe 12 then suctions the internal standard substance and discharges the suctioned substance into the solid phase extraction cartridge 3 containing the equilibrated solid phase extraction agent.

After this, the sample probe 12 moves to a position over the rack 20 that has been carried by the sample transport mechanism 19, then suctions the sample from the sample container 21, and discharges the sample into the solid phase extraction cartridge 3 set up in the cartridge transport means 1. At the same time, the solution inside the cartridge 3 formed as a mixture of the sample and the internal standard substance, is repeatedly suctioned and discharged a plurality of times for stirring.

The sample probe 12 next moves to a position over a discarding port 22 and throws away the tip 18 that has been used. The cartridge transport means 1 then rotates for the cartridge holder 4 holding the solid phase extraction cartridge 3 to reach position B. At this time, similarly as above, the cartridge holders 4 and the receiving tray holders 6 move maintaining the respective relative positions.

The pressure loader 7 positioned over positions B and D, moves downward to the cartridge holder 4 at position B and applies an air pressure load to pass the sample and the internal standard substance into the solid phase extraction cartridge 3 in which the substance to be assayed is then retained in the solid phase extraction agent. The passed sample solution will remain in the receiving tray 5.

Next, the washing step to pass water through the solid phase extraction agent is described below. The cartridge transport means 1 rotates for the cartridge holder 4 holding the solid phase extraction cartridge 3 to reach position C. At this time, similarly as above, the cartridge holders 4 and the receiving tray holders 6 move maintaining the respective relative positions. After this, the water-based solvent probe 13 discharges water into the solid phase extraction cartridge 3 holding the substance to be assayed (analyte).

The cartridge transport means 1 then rotates for the cartridge holder 4 holding the solid phase extraction cartridge 3 to reach position D. At this time, similarly as above, the cartridge holders 4 and the receiving tray holders 6 move maintaining the respective relative positions. The pressure loader 7 positioned over positions B and D, moves downward to the cartridge holder 4 at position D and applies an air pressure load to pass the water into the solid phase extraction cartridge 3 in which the solid phase extraction agent is then washed. The passed water will remain in the receiving tray 5.

Next, the step of passing an organic solvent through the solid phase extraction agent and eluting the analyte from the solid phase extraction agent is described below. The cartridge transport means 1 rotates until the cartridge holder 4 holding the solid phase extraction cartridge 3 reaches position A. At this time, similarly as above, the cartridge holders 4 and the receiving tray holders 6 move maintaining the respective relative positions.

The receiving tray transport arm 11 moves the receiving tray 5 with the waste liquid collected therein, to a position over a discarding port 22, and discards the tray 5 therefrom. The receiving tray transport arm 11 next moves to a position over the receiving tray storage unit 10 and mounts a new receiving tray 5 in the receiving tray holder 6.

The organic solvent probe 14 next discharges methanol into the solid phase extraction cartridge 3 containing the above-washed solid phase extraction agent. The cartridge transport means 1 rotates until the cartridge holder 4 holding the solid phase extraction cartridge 3 reaches position B. At this time, similarly as above, the cartridge holders 4 and the receiving tray holders 6 move maintaining the respective relative positions.

The pressure loaders 7 positioned over positions B and D, moves downward to the cartridge holder 4 at position B and applies an air pressure load to pass the methanol into the solid phase extraction cartridge 3 in which the substance to be assayed is then eluted. The eluted substance is collected in the receiving tray 5.

The above process steps can be described more simply as follows. During solid phase extraction agent conditioning, an organic solvent is added to a solid phase extraction cartridge 3 at position A (1st substep). At position B, the organic solvent is passed through the solid phase extraction agent by a pressure load (2nd substep). At position C, a water-based solvent is added to the solid phase extraction cartridge 3 (3rd substep). At position D, the water-based solvent is passed through the solid phase extraction agent by a pressure load (4th substep).

Next, the transport means 1 rotates from position D to position A at which a reagent and a sample are then added to the solid phase extraction cartridge 3 (5th substep). At position B, the sample is retained in the solid phase extraction agent by a pressure load (6th substep). At position C, water-based solvent is added to the solid phase extraction cartridge 3 (7th substep). At position D, the water-based solvent is passed through the solid phase extraction agent by a pressure load (8th substep).

After this, the transport means 1 rotates from position D to position A at which organic solvent is then added to the solid phase extraction cartridge 3 (9th substep). At position B, the target substance in the solid phase extraction agent is eluted by a pressure load (10th substep) and then is collected in the receiving tray 5.

As described above, the 10 process substeps are executed at positions A to D by the rotation of the cartridge holder 1 and receiving tray transport means 2 and the operation of the probes 12 to 14 and pressure loaders 7.

Next, the measuring step in the mass analytical unit 27 is described below. The cartridge transport means 1 rotates until the cartridge holder 4 holding the solid phase extraction cartridge 3 has reached position C. At this time, similarly as above, the cartridge holders 4 and the receiving tray holders 6 move maintaining the respective relative positions.

After this, the analyte-containing eluate in the receiving tray 5 is suctioned by the eluate probe 23, and then is injected into the eluate injection port 25. The eluate injection port 25 is positioned on a flow path to which a solution is supplied from the pump 24. With this flow injection analysis (FIA) method, the analyte reaches the ionizer 26, and then is ionized under a high-temperature and high-voltage atmosphere, and then is introduced into the mass analytical unit 27.

The FIA method, where the sample is introduced into a flow path to which a solution is supplied from the pump 24, requires significantly shorter time compared to normal high-performance liquid chromatography/mass spectrometry (LC/MS) method. In the FIA method, however, a plurality of constituents of the sample are introduced into the mass analyzer at the same time, because there is no column for separating them.

Using a 70% methanol solution containing 10 mM of ammonium formate as a solvent, the solution is sent at a flow velocity of 100 microliters/min. For the mass analytical unit 27, an MRM (Multiple Reaction Monitoring) mode of a highly selective triple-quadrupole mass analyzer is used, where the analysis time is set to 2 minutes.

The MRM mode is a method such that only a precursor signal is passed through using a quadrupole of a first stage, then the signal is fragmented in a next collision cell, and then only a product signal specific to the generated chemical compound is monitored using a quadrupole of a second stage. This method enables identification of a chemical compound with specific mass information relating to the compound. The mass analytical unit 27 can use any one of an ion trap mass analyzer, a time-of-flight mass analyzer, a quadrupole mass analyzer, and a Fourier transform mass analyzer, instead of a triple-quadrupole mass analyzer.

Next, the cartridge transport means 1 rotates for the cartridge holder 4 holding the solid phase extraction cartridge 3 to reach position D, and then a pressure loader 7 applies an air pressure load. After this, the cartridge transport means 1 further moves to make the cartridge holder 4 holding the solid phase extraction cartridge 3 reach position A. The cartridge transport arm 9 and the receiving tray transport arm 11 then move the solid phase extraction cartridge 3 and the receiving tray 5, respectively, to positions over respective discarding ports 22 and discard the solid phase extraction cartridge 3 and the receiving tray 5, respectively.

Upon completion of discarding, the cartridge transport arm 9 and the receiving tray transport arm 11 move to a position over the cartridge storage unit 9 and the receiving tray storage unit 10, and mount a new solid phase extraction cartridge 3 and a new receiving tray 5, respectively, in the cartridge holder 4 and the receiving tray holder 6, respectively.

In the first embodiment, the cartridge holders 4 are located in four places and the pressure loaders 7 in two places. In addition, the pressure loading positions B and D, and the sample and solvent adding positions A and C (where the cartridge holders 4 are not positioned under the pressure loaders 7) are located alternately on a circumference of the cartridge transport means 1, which is a rotating body. The positions at which sample addition, solvent addition, and pressure loading are conducted, therefore, can each be changed by rotating the cartridge transport means 1. This rotation allows sample addition, solvent addition, and pressure loading to be executed continuously. This in turn reduces probe and arm moving distances, enhances access efficiency, and simplifies mechanisms.

Regarding sample and solvent adding positions A and C, organic solvent is always added at the solvent adding position A, and water-based solvent is always added at solvent adding position C, in accordance with the progress pattern of the solvent extraction steps. Therefore, the solvent probes can be arranged such that the water-based solvent probe 13 is set for water-based solvent use only, and the organic solvent probe 14 is set for organic solvent use only. Furthermore, the probes 13 and 14 require no movement other than rotation or vertical movement for suctioning/discharging operations.

Figure 5:
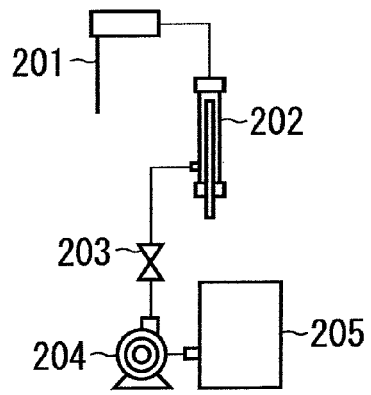
FIG. 5 is a conceptual diagram of a probe for solvent use in the embodiment of the present invention.

As shown in FIG. 5, each of the water-based solvent probe 13 and the organic solvent probe 14 includes a reservoir tank 205 for storage of a solvent, a pump 204 that supplies the solvent, a feed water valve 203, a syringe mechanism 202 that suctions an appropriate amount of solvent, and a probe 201 that discharges the solvent.

The geometric size and the cost of the apparatus is reduced because of the simplified probe configuration, where the discharging position is fixed, requiring no movement for the probes 13, 14. The probes are further simplified because each probe is used for a dedicated solvent, rendering it unnecessary to exchange probe tips for undedicated solvents.

Figure 6:
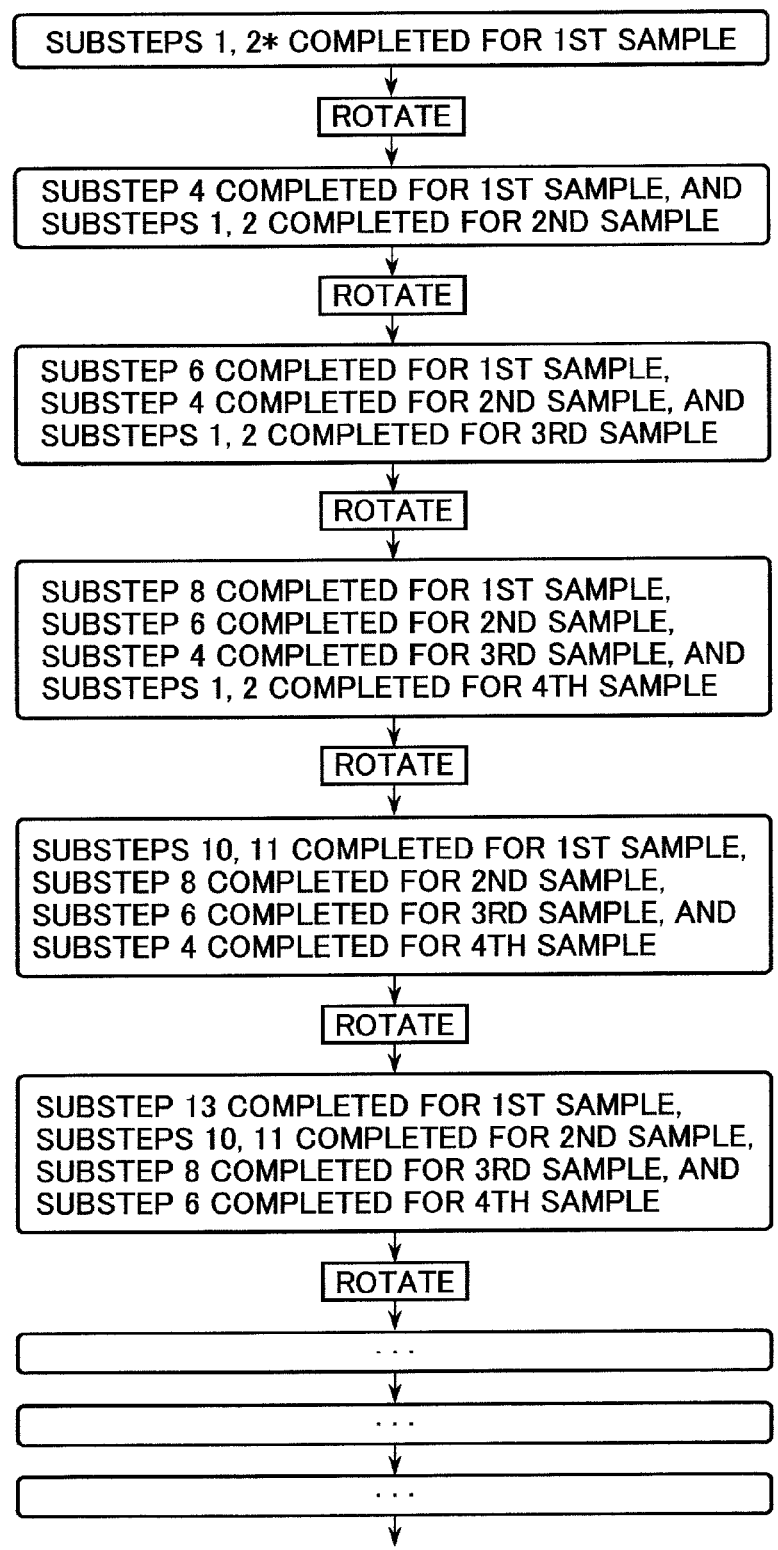
FIG. 6 is a conceptual diagram that represents only rotation timing in the progress pattern of the analytical steps executed simultaneously/concurrently in the embodiment of the present invention.

In addition, the alternate layout of the solvent adding positions and pressure loaders in the first embodiment of the present invention enables four types of operation to be simultaneously processed in parallel and hence improves throughput. More specifically, as shown in FIG. 6, in order to process a first sample, one solid phase extraction cartridge 3 and one receiving tray 5 are mounted, and then methanol is added, and then after the cartridge transport means 1 rotates them to position B, processing of a second sample can now be started.

Similarly, processing of a third sample can be started after the first sample has arrived at position C and the second sample at position B. The same also applies to a fourth sample. For simultaneous parallel processing, as shown in FIG. 6, the cartridge transport means 1 starts rotating after all process substeps of each sample currently undergoing concurrent processing have been completed.

Additionally, the amount of solution to be used is minimized and costs are reduced. For example, the volume of liquid solutions required during solid-phase extraction of one sample are 400 microliters (200 microliters×2) of methanol, 400 microliters (200 microliters×2) of water, 100 microliters of the sample, and 10 microliters of internal standard substance. Total solution consumption, inclusive of a quantity required for mass analysis, can be minimized to nearly 1 milli-liter. Cost reduction is therefore achievable and a waste liquid volume is also small. In addition, waste liquid processing costs can be reduced.

Figure 7:
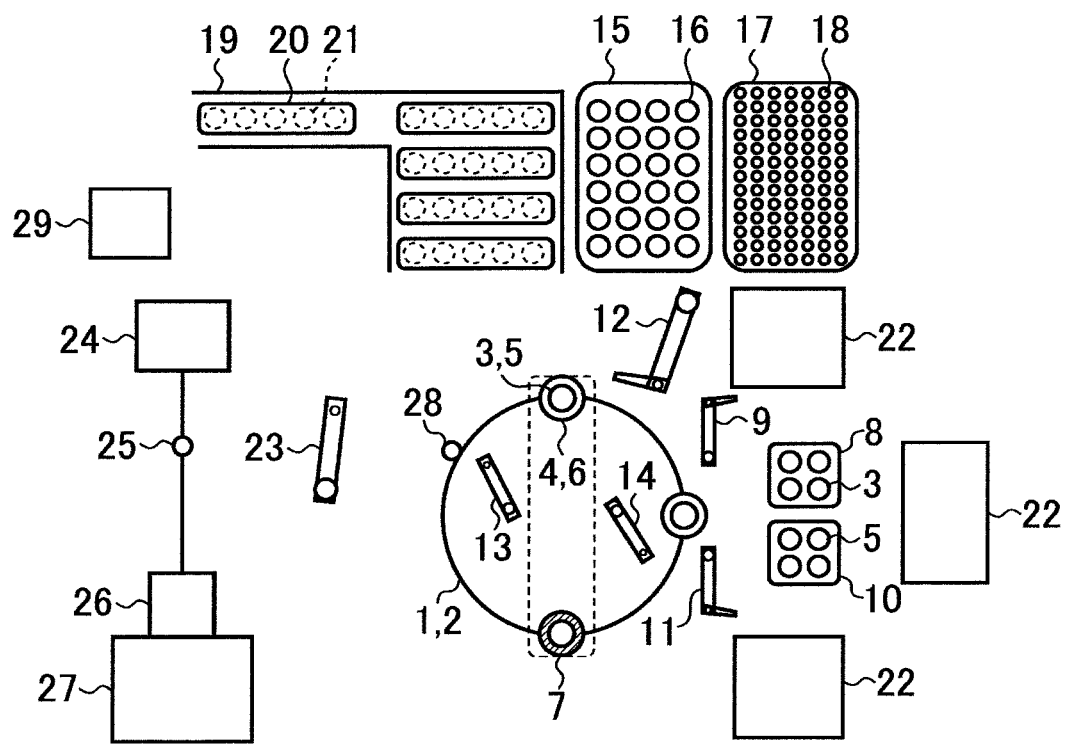
FIG. 7 shows a variant of the embodiment according to the present invention, the figure being a conceptual diagram of an apparatus configuration including two positions for cartridge holders and one position for a pressure loader.

The apparatus configuration in the first embodiment of the present invention includes the cartridge holders 4 in four places and the pressure loaders 7 in two places. The number of cartridge holders 4 and pressure loaders 7 becomes a factor in both dimensional reduction of the apparatus and the improvement of its throughput, both of which tend to conflict with each other. To assign priority to dimensional reduction, it is appropriate for the apparatus to include, for example, cartridge holders 4 in two places and a pressure loader 7 in one place, as shown in FIG. 7. In this configuration, parallel processing is impossible, so that throughput decreases, and since reagent and solvent addition is limited to one place, the necessity arises to undertake preventive measures against movement interference between the probes and the arms during movement.

Figure 8:
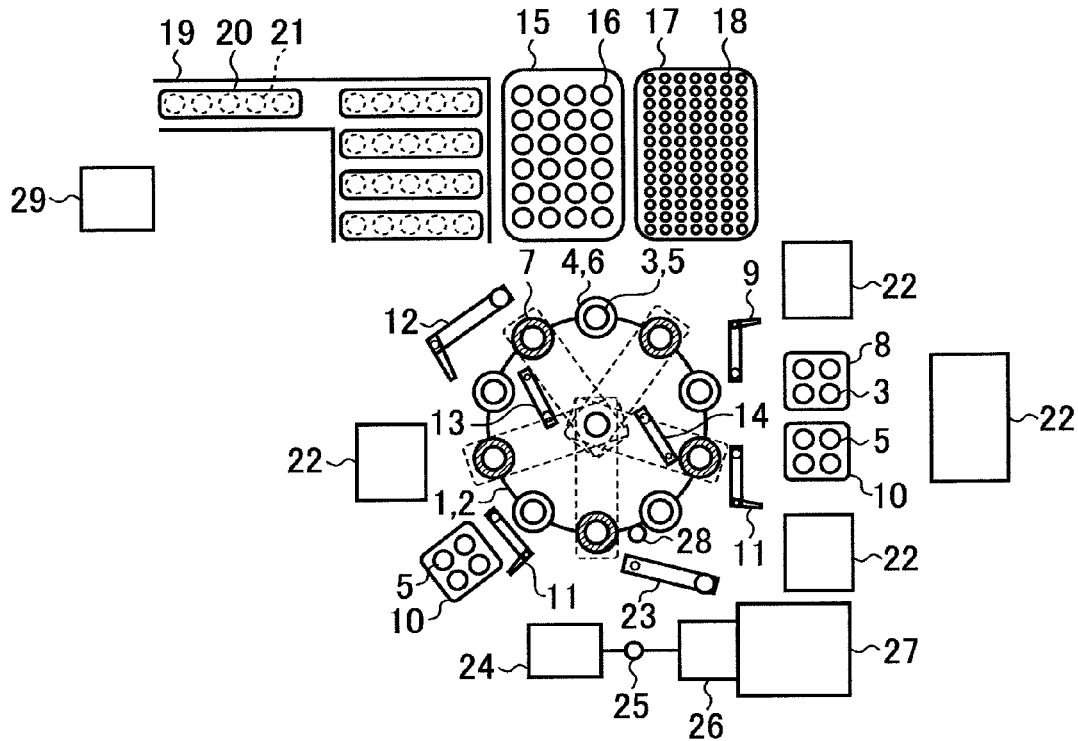
FIG. 8 shows another variant of the embodiment according to the present invention, the figure being a conceptual diagram of an apparatus configuration including ten positions for cartridge holders and five positions for pressure loaders.

Conversely, to assign priority to the improvement of throughput, apparatus configuration with, for example, the cartridge holders 4 in ten places and the pressure loaders 7 in five places, is appropriate. This configuration is shown in FIG. 8. In this configuration, although the successive solid-phase extraction substeps are completed while the cartridge transport means 1 rotates one full turn, the receiving tray storage units 10, the receiving tray transport arms 11, and the discarding ports 22 need to be arranged in a number of places. In addition, since the positions for adding water and methanol are not at a fixed position, the water-based solvent probe 13 and the organic solvent probe 14 need to have a movable solvent-adding position. This increases an installation area of the apparatus and makes both the apparatus and individual parts complex in configuration.

Figure 9:
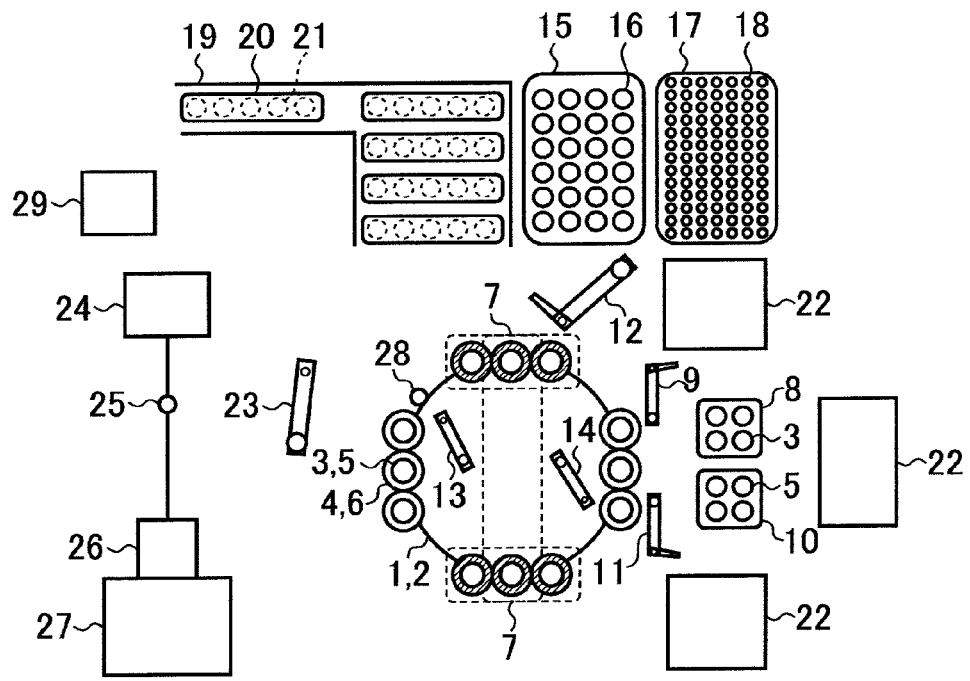
FIG. 9 shows yet another variant of the embodiment according to the present invention, the figure being a conceptual diagram of an apparatus configuration including a multiple cartridge-holder structure.

To prioritize the improvement of throughput, it may also be necessary that each cartridge holder 4 in the first embodiment of the present invention be modified into a multiple (in the illustrated example, triple) holder arrangement as shown in FIG. 9. The holder arrangement shown in FIG. 9 is expected to improve throughput without increasing the apparatus installation area, and allow each of the water-based solvent probe 13 and the organic solvent probe 14 to have a fixed respective solvent-adding position. Although FIG. 9 shows a triple holder arrangement as an example, any arrangement with holders equal to or more than two holders (i.e., a double) may be adopted instead.

Furthermore, for enhanced purity of samples in the present embodiment, extraction is repeated a plurality of times using solid phase extraction cartridges of different modes. For example, a cartridge of a first stage is used for extraction in ion exchange mode and a cartridge of a second stage is used for in reverse-phase mode. Thus, purity improves and even for samples with differences between individuals, data reliability also improves. In this case, a substep progress pattern different from normal one is applied to such repetition of. In a normal substep progress pattern, the process completes after the cartridge transport means 2 rotates three full turns, whereas to complete this multiple extraction process, the cartridge transport means 2 rotates six full turns.

As described above, the four cartridge holders 4 are positioned at an equal spacing in the cartridge transport means 1 adapted to carry the cartridge holders along the continuous track surface, and the two pressure loaders 7 are positioned over a pair of mutually corresponding cartridge holders 4 on the cartridge transport means 1. This layout enables the automatic analyzer to repeatedly execute the five substeps of solid-phase extraction, suppress expenditure cost associated with consumable materials, and conduct the successive solid-phase extraction substeps efficiently for separation and purification of multiple analytes. The above layout also makes the apparatus more compact and enhances throughput.

While the circular cartridge transport means 1 and circular receiving tray transport means 2 in the above embodiment are constructed to rotate about the same rotational axis so that one cartridge holder 4 and one receiving tray holder 6 face each other in a vertical direction, the circular cartridge transport means 1 and the circular receiving tray transport means 2 can also be constructed to rotate about rotational axes different from each other.

In that case, the configuration may be such that the circular cartridge transport means 1 and the circular receiving tray transport means 2 are arranged in an offset condition relative to each other. For example, at position B of the cartridge transport means 1, the cartridge holder 4 and the receiving tray holder 6 in the receiving tray transport means 2 face each other in the vertical direction, while the holders 4 and 6 do not face each other at other positions, namely positions A, C, and D.

That is to say, in this configuration, a receiving tray 5 held by a receiving tray holder 6 in a receiving tray transport means 2 collects the extract of the analyte, which will be eluted from a solid phase extraction cartridge 3 in a cartridge holder 4, while a container other than a receiving tray 5 collects the solvent(s) used during solid phase extraction agent conditioning.

In such an offset configuration, design flexibility of the eluate removal probe 23 can be increased with an open space left over the receiving tray transport means 2.

DESCRIPTION OF REFERENCE NUMBERS

1 . . . Cartridge transport means, 2 . . . Receiving tray transport means, 3 . . . Solid phase extraction cartridges, 4 . . . Cartridge holders, 5 . . . Receiving trays, 6 . . . Receiving tray holders, 7 . . . Pressure loaders, 8 . . . Cartridge storage unit, 9 . . . Cartridge transport arm, 10 . . . Receiving tray storage unit, 11 . . . Receiving tray transport arm, 12 . . . Sample probe, 13 . . . Water-based solvent probe, 14 . . . Organic solvent probe, 15 . . . Reagent storage unit, 16 . . . Reagent containers, 17 . . . Tip storage unit, 18 . . . Dispensing tips, 19 . . . Sample transport mechanism, 20 . . . Rack, 21 . . . Sample containers, 22 . . . Discarding ports, 23 . . . Eluate probe, 24 . . . Pump, 25 . . . Eluate injection unit, 26 . . . Ionizer, 27 . . . Mass analytical unit, 28 . . . Washing port, 29 . . . Control unit, 101 . . . Automatic analyzer, 102 . . . Computer, 103 . . . A/D converter, 104 . . . Printer, 105 . . . LCD with touch panel, 106 . . . Memory, 107 . . . Syringe mechanism, 108 . . . Pump mechanism, 109 . . . Interface, 110 . . . Arm driving mechanism, 111 . . . Transport means driving mechanism, 112 . . . Pressure loader driving mechanism, 201 . . . Probe, 202 . . . Dispensing mechanism, 203 . . . Feedwater valve, 204 . . . Pump, 205 . . . Tank

The invention claimed is:

1. A biological sample preprocessing apparatus, comprising:
   solid-phase extraction cartridges that each purify/concentrate specific constituents of a biological sample;
   cartridge holders that each hold one of the solid-phase extraction cartridges;
   cartridge transport means that carries the cartridge holders along a continuous track surface thereof;
   a sample probe that discharges the biological sample into the solid-phase extraction cartridge held in one of the cartridge holders;
   a water-based solvent probe that discharges a water-based solvent into the solid-phase extraction cartridge held in the cartridge holder;
   an organic solvent probe that discharges an organic solvent into the solid-phase extraction cartridge held in the cartridge holder;
   a pressure loader that applies an pressure load to the solid-phase extraction cartridge held in the cartridge holder;
   an elute probe that suctions/discharges a eluted extract and introduced the eluate into a mass analyzer;
   a washing port that washes the eluate probe;
   a receiving tray transport means configured to carry receiving tray holders along a continuous track surface thereof, the receiving tray transport means and the cartridge transport means rotating about a first rotational axis, the cartridge transport means being disposed over the receiving tray transport means, and the washing port being disposed at a point on an edge of the receiving tray transport means; and
   a controller that controls operation of the cartridge transport means, the sample probe, the water-based solvent probe, the organic solvent probe, the eluate probe, and the pressure loader;
   wherein the cartridge holders are located in four places and the pressure loaders in two places, and the pressure loading positions B and D, and the sample and solvent adding positions A and C are located alternately on a circumference of the cartridge transport means, which is a rotating body;

wherein the controller is configured to perform:

a procedure of transporting the solid-phase extraction cartridge and a receiving tray to a cartridge storage unit and a receiving tray storage unit;

a procedure of discharging the organic solvent into the solid-phase extraction cartridge at the position A;

a procedure of rotating the solid-phase extraction cartridge to the position B by the cartridge transport means;

a procedure of applying a pressure in the solid-phase extraction cartridge by the pressure loader at the position B;

a procedure of rotating the solid-phase extraction cartridge to the position C by the cartridge transport means;

a procedure of discharging the water-based solvent into the solid-phase extraction cartridge at the position C;

a procedure of rotating the solid-phase extraction cartridge to the position D by the cartridge transport means;

a procedure of applying a pressure in the solid-phase extraction cartridge by the pressure loader at the position D;

a procedure of rotating the solid-phase extraction cartridge to the position A by the cartridge transport means;

a procedure of discharging a sample and an internal standard substance into the solid-phase extraction cartridge at the position A;

a procedure of rotating the solid-phase extraction cartridge to the position B by the cartridge transport means;

a procedure of applying a pressure in the solid-phase extraction cartridge by the pressure loader at the position B;

a procedure of rotating the solid-phase extraction cartridge to the position C by the cartridge transport means;

a procedure of discharging the water-based solvent into the solid-phase extraction cartridge at the position C;

a procedure of rotating the solid-phase extraction cartridge to the position D by the cartridge transport means;

a procedure of rotating the solid-phase extraction cartridge by the pressure loader at the position D;

a procedure of rotating the solid-phase extraction cartridge to the position A by the cartridge transport means;

a procedure of discharging the organic solvent into the solid-phase extraction cartridge at the position A;

a procedure of rotating the solid-phase extraction cartridge to the position B by the cartridge transport means;

a procedure of applying a pressure in the solid-phase extraction cartridge by the pressure loader at the position B;

a procedure of rotating the solid-phase extraction cartridge to the position C by the cartridge transport means;

a procedure of injecting an analyte-containing eluate into an eluate injection port by the eluate probe at the position C; and a procedure of discarding the solid-phase extraction cartridge and the receiving tray.

2. A mass analyzing apparatus comprising: an eluate injection unit that introduces specific constituents of a biological sample eluted from the biological sample preprocessing apparatus according to claim 1; and a mass analytical unit that analyzes a mass of the eluate injected into the eluate injection unit.

3. The biological sample preprocessing apparatus according to claim 1, wherein: the cartridge transport means is circular, and a series of process steps are completed while the cartridge transport means rotates through three full turns.

\* \* \* \* \*